US008594945B2

(12) United States Patent
Lee et al.

(10) Patent No.: US 8,594,945 B2
(45) Date of Patent: Nov. 26, 2013

(54) METHOD OF IMPROVEMENT OF ORGANISMS USING PROFILING THE FLUX SUM OF METABOLITES

(75) Inventors: Sang-Yup Lee, Daejeon (KR); Tae Yong Kim, Gyeonggi-do (KR); Dong-Yup Lee, Gyeonggi-do (KR)

(73) Assignee: Korea Advanced Institute of Sciecnce and Technology, Daejeon (KR)

( * ) Notice: Subject to any disclaimer, the term of this patent is extended or adjusted under 35 U.S.C. 154(b) by 651 days.

(21) Appl. No.: 12/299,223

(22) PCT Filed: Sep. 8, 2006

(86) PCT No.: PCT/KR2006/003576
§ 371 (c)(1),
(2), (4) Date: Mar. 13, 2009

(87) PCT Pub. No.: WO2007/129793
PCT Pub. Date: Nov. 15, 2007

(65) Prior Publication Data
US 2009/0305328 A1    Dec. 10, 2009

(30) Foreign Application Priority Data

May 4, 2006    (KR) .......................... 10-2006-0040552

(51) Int. Cl.
*G06F 19/12*    (2011.01)
(52) U.S. Cl.
CPC ..................................... *G06F 19/12* (2013.01)
USPC ........................................................... 702/19
(58) Field of Classification Search
CPC ....................................................... G06F 19/12
See application file for complete search history.

(56) References Cited

U.S. PATENT DOCUMENTS

2002/0142321 A1* 10/2002 Palsson et al. ................... 702/19
2002/0168654 A1* 11/2002 Maranas et al. .................. 435/6

(Continued)

OTHER PUBLICATIONS

Lee, S.J.Y., Lee, D.-yup, Kim, T.Y.Y., Kim, B.H.H. & Lee, J. Metabolic engineering of *Escherichia coli* for enhanced production of succinic acid, based on genome comparison and in silico gene knockout simulation. Applied and Environmental Microbiology 71, 7880-7887 (2005).*

(Continued)

*Primary Examiner* — Soren Harward
(74) *Attorney, Agent, or Firm* — Tristan A. Fuierer; Andrew D. Gerschutz; Moore & Van Allen, PLLC

(57) ABSTRACT

The present invention relates to a method for improving an organism through the profiling of flux sum of metabolites, and more particularly to a method for screening key metabolites, the method comprises: plotting a profile between objective functions based on useful substance formation rate as a main function through an algorithm perturbing other functions influencing the production of useful substance; determining the utilization (flux sum ($\Phi$)) of all metabolites from the profile; and screening key metabolites, which show an increase in flux sum ($\Phi$) with an increase in useful substance formation rate. The present invention also relates to a method for improving an organism producing a useful substance, the method comprises introducing and/or amplifying genes associated with the screened key metabolites or introducing the genes from the outside into the organism. According to the disclosed invention, the metabolic utilization (flux sum; $\Phi$) of specific metabolites according to an increase in useful substance formation rate can be predicted, so that key metabolites in increasing the production of a useful substance can be screened. Also, it is possible to increase the production of a useful substance through the method of improving a target organism by introducing and/or amplifying genes associated with the screened metabolites or through the method of supplying the metabolites during the culture of the organism.

6 Claims, 4 Drawing Sheets

(56) References Cited

U.S. PATENT DOCUMENTS

2005/0079482 A1* 4/2005 Maranas et al. .................. 435/4
2005/0221278 A1* 10/2005 Iwatani et al. .................. 702/19

OTHER PUBLICATIONS

Varma, A., Boesch, B.W., Palsson, B.O. & Paisson, B. Biochemical production capabilities of *Escherichia coli*. Biotechnology and Bioengineering 42, 59-73 (1993).*

Lee, Sang Yup, et al., Systems biotechnology for strain improvement, Trends in Biotechnology, Jul. 2005, p. 349, vol. 23, issue 7.
Papin, Jason A., et al., Reconstruction of cellular signalling networks and analysis of their properties, Nature Reviews Molecular Cell Biology, Feb. 2005, p. 99, vol. 6.
Neidhardt, Frederick C., et al., *Escherichia coli* and Salmonella: Cellular and Molecular Biology, 1996, vol. 1.
Pharkya, Priti, et al., Exploring the Overproduction of Amino Acids Using the Bilevel Optimization Framework OptKnock, Biotechnol Bioeng., 2003, pp. 887-899, vol. 84.

* cited by examiner

METHOD OF IMPROVEMENT OF ORGANISMS USING PROFILING THE FLUX SUM OF METABOLITES

CROSS-REFERENCE TO RELATED APPLICATIONS

This application is filed under the provisions of 35 U.S.C. §371 and claims the priority of International Patent Application No. PCT/KR2006/003576 filed on 8 Sep. 2006 entitled "Method of Improvement of Organisms Using Profiling the Flux Sum of Metabolies" in the name of Sang-Yup Lee, et al., which claims priority of Korean Patent Application No. 10-2006-0040552 filed on 4 May 2006, both of which are hereby incorporated by reference herein in their entirety.

TECHNICAL FIELD

The present invention relates to a method for improving an organism through the profiling of flux sum of metabolites, and more particularly to a method for screening key metabolites, the method comprises; plotting a profile between objective functions based on useful substance formation rate as a main function through an algorithm perturbing other functions influencing the production of useful substance; determining the utilization (flux sum ($\Phi$)) of all metabolites from the profile; and screening key metabolites, which show an increase in flux sum ($\Phi$) with an increase in useful substance formation rate. The present invention also relates to a method for improving an organism producing a useful substance, the method comprises introducing and/or amplifying genes associated with the screened key metabolites or introducing the genes from the outside into the organism.

BACKGROUND ART

There have been many efforts to alter the metabolic characteristics of cells or strains in the desired direction by introducing new metabolic pathways or deleting, amplifying or modifying the existing metabolic pathways using molecular biological technology related to genetic recombination technology. With the aid of bioinformatics, which has been newly developed and increasingly used, the construction of each metabolic network model became possible, and thus it became possible to improve organisms to have various characteristics, including the overproduction of existing metabolites, the production of novel metabolites, inhibition of production of unfavorable metabolites, utilization of various substrates, degradation of non-biodegradable compounds.

However, currently, improvement of strains is performed mainly by methods, such as the over-expression of one or two enzymes or the introduction or deletion of simple metabolic pathways, but in many cases, the results was not as good as desired. In addition, metabolically improved strains can hardly be used in the production of substances that require changes in complex metabolic fluxes. It is known that one reason is because strains themselves generally tend to grow rather than to produce desired useful substances. Specifically, because strains have evolved that they would synthesize substances required for the growth of the strains themselves in the most optimized way, efforts to produce specific useful substances inevitably compete with these strains having a tendency to grow.

Another reason why the theoretical yield is not achieved is that complex metabolic pathways could not be correctly understood. Specifically, genetic recombination technology for the manipulation of metabolic pathways and the introduction of metabolic pathways has been significantly developed, whereas techniques for analysis and prediction through metabolic pathways have just recently showed the possibility with rapidly increasing genomic information. In particular, the metabolic pathway model of each of microorganisms is combined with mathematical models and optimization technology, and thus it is becoming possible to predict metabolic pathway reactions occurring after the deletion or addition of genes (Lee et al., *Trends Biotechnol.*, 23:349, 2005).

It is known that metabolic flux analysis techniques show the ideal metabolic fluxes of cells and allow exact simulation and prediction of the behavior of cells, even though they do not require dynamic information (Papin, J. et al., *Nature Reviews Molecular Cell Biology*, 6:99, 2005). Metabolic flux analysis aims to determine an ideal metabolic flux space that cells can reach using only mass balance of biochemical reactions and information on cell composition, and to maximize or minimize specific objective functions through an optimization method (e.g., the maximization of biomass formation rate or the minimization of metabolic regulation by specific perturbation). In addition, metabolic flux analysis can be generally used to calculate the maximum production yield of the desired metabolite through strain improvement and the determined value can be used to understand the characteristics of metabolic pathways in strains. Also, various studies, which utilize the metabolic flux analysis technique to predict metabolic flux changes occurring after the deletion or addition of genes, have been reported.

In view of this, there is an urgent need to develop a method, which can explain the complex metabolism of microorganisms using the metabolic flux analysis technique from an overall point of view other than strain manipulation that uses partial metabolic information, which can provide an understanding of the effects of manipulation of a specific gene on the overall metabolic flux, and which can scientifically test and accurately predict the optimal microbial metabolic fluxes required for the mass production of target useful substances.

Accordingly, the present inventors have made many efforts to find a method for efficiently increasing the production of target useful substances, and as a result, found that specific key metabolites involved in the production of the useful substances can be identified by plotting a profile of an objective function through an algorithm that perturbs functions involved in the formation rate and production of the useful substances, determining the utilization (defined as flux sum ($\Phi$)) of each metabolite from the profile, and screening key metabolites, from the profile. The key metabolites that show an increase in flux sum ($\Phi$) value according to an increase in the formation rate of the useful substances, thereby complete the present invention.

SUMMARY OF THE INVENTION

A main object of the present invention is to provide a method for screening specific key metabolites that increase the production yield of a useful substances, the method comprising plotting a profile relating to a single objective function through an algorithm perturbing one or more functions involved in the formation rate and production of the useful substances, and determining the metabolite utilization (defined as flux sum ($\Phi$)) of an organism from the profile.

Another object of the present invention is to provide a method for improving an organism producing useful substances, the method comprising introducing and/or amplifying genes associated with the aforementioned screened specific metabolite.

Still another object of the present invention is to provide a method for preparing a useful substance, in which genes associated with the screened specific metabolites are supplied during the culture of an organism producing the useful substances.

To achieve the above objects, in one aspect, the present invention provides a method for screening key metabolites involved in increasing the production of useful substances, the method comprising the steps of: (a) selecting a target organism for producing a target useful substance, and constructing the metabolic network model of the selected organism; (b) defining the utilization of each metabolite as flux sum ($\Phi$) represented by Equation 1 below, and plotting a profile of a single objective function relating to the formation rate of the useful substance by perturbing one or more functions involved in the formation rate and production of the useful substances through flux sum SCOF (flux sum scanning with compromised objective fluxes), in order to determine flux sum on the metabolic pathway constructed in the step (a); (c) determining the flux sum ($\Phi$) of each of metabolites from the profile plotted through the flux sum SCOF; and (d) clustering and screening a specific metabolite which show an increase in flux sum ($\Phi$) according to an increase in the formation rate of the target useful substance:

$$\Phi_i = |f_{in}| = |f_{out}| = 1/2 \sum_j |S_{ij} v_j| \qquad \text{[Equation 1]}$$

wherein $\Phi_i$ represents the utilization of the $i^{th}$ metabolite, $f_{in}$, represents the metabolic flux of a reaction where a relevant metabolite is consumed with respect to the $i^{th}$ metabolite, $f_{out}$ represents the metabolic flux of a reaction where the useful target substance is produced with respect to the $i^{th}$ metabolite, $S_{ij}$ represents the stoichiometric coefficient of the $i^{th}$ metabolite in the $j^{th}$ reaction, and $v_j$ represents the metabolic flux vector of the $j^{th}$ pathway.

In another aspect, the present invention provides a method for improving an organism producing a useful substance, the method comprising the steps of: (a) selecting a target organism for producing a target useful substance, and constructing the metabolic network model of the selected organism; (b) defining the utilization of each metabolite as flux sum ($\Phi$) represented by Equation 1 below, and plotting a profile of a single objective function relating to the formation rate of the useful substance by perturbing one or more functions involved in the formation rate and production of the useful substances through flux sum SCOF (flux sum scanning with compromised objective fluxes), in order to determine flux sum on the metabolic pathway constructed in the step (a); (c) determining the flux sum ($\Phi$) of each of metabolites from the profile plotted through the flux sum SCOF; (d) clustering and screening a specific metabolite which show an increase in flux sum ($\Phi$) according to an increase in the formation rate of the target useful substances; (e) selecting genes to be amplified from a metabolic pathway associated with the specific metabolites screened in the step (d); and (f) constructing a mutant of the target organism by introducing and/or amplifying the genes selected in the step (e) in the target organism.

The method for improving the organism producing the useful substance may additionally comprises a step of: (g) experimentally confirming the production of the useful substance by culturing the mutant constructed in the step (f).

In still another aspect, the present invention provides a method for preparing a useful substance, the method comprising culturing an organism improved according to said improvement method.

In yet another aspect, the present invention provides a method for preparing a useful substance by culturing an organism, the method comprises supplying the screened metabolites during the culture of the organism, wherein the metabolites are obtained by the steps of: (a) selecting a target organism for producing a target useful substance, and constructing the metabolic network model of the selected organism; (b) defining the utilization of each metabolite as flux sum ($\Phi$) represented by Equation 1 below, and plotting a profile of a single objective function relating to the formation rate of the useful substance by perturbing one or more functions involved in the formation rate and production of the useful substances through flux sum SCOF (flux sum scanning with compromised objective fluxes), in order to determine flux sum on the metabolic pathway constructed in the step (a); (c) determining the flux sum ($\Phi$) of each of metabolites from the profile plotted through the flux sum SCOF; and (d) clustering and screening specific metabolites which show an increase in flux sum ($\Phi$) according to an increase in the formation rate of the target useful substances.

In the present invention, the function in the step (b) in the process of screening the metabolites is preferably one or more selected from the group consisting of specific growth rate, byproduct formation rate, substrate uptake rate, ATP formation rate and oxygen uptake rate. Also, the flux sum SCOF in the step (b) comprises determining the minimum value and maximum value of each of objective functions other than the formation rate of the useful substance, and performing optimization while increasing the formation rate of the useful substance within a range between the minimum value and the maximum value.

In the present invention, $f_{in}$ and $f_{out}$, are preferably represented by Equations 2 and 3 below, respectively:

$$f_{in} = \sum_j^{ingoing} |S_{ij} v_j| \qquad \text{[Equation 2]}$$

$$f_{out} = \sum_j^{outgoing} |S_{ij} v_j| \qquad \text{[Equation 3]}$$

wherein $S_{ij}$ represents the stoichiometric coefficient of the $i^{th}$ metabolite in the $j^{th}$ reaction, and $v_j$ represents the metabolic flux vector of the $j^{th}$ pathway.

In the present invention, the target organism is preferably a microorganism. Also, the useful target substance is a primary metabolite, a secondary metabolite or a foreign protein, and the target organism is a microorganism capable of producing a primary metabolite, a secondary metabolite or a foreign protein.

Other features and embodiments of the present invention will be more fully apparent from the following detailed description and appended claims.

BRIEF DESCRIPTION OF DRAWINGS

In FIG. 2, $f_{in}$ consists of three metabolic fluxes, and $f_{out}$ consists of two metabolic fluxes.

DETAILED DESCRIPTION OF THE INVENTION, AND PREFERRED EMBODIMENTS THEREOF

As used herein, the term "perturbation" refers to a manipulation perturbing a group of all metabolites by the application of a specific external factor so as to find a metabolite having the desired property.

As used herein, the term "clustering" is intended to include a method and process of grouping metabolites showing similar patterns from a group of metabolites resulting from perturbation of all metabolites.

As used herein, the "amplification" of genes encompasses all operations of increasing the expression levels of the relevant genes by manipulating all or part of the base sequences of the genes to be replicated in an organism in large amounts.

As used herein, the term "culture" is defined to encompass not only the culture of microorganisms, such as bacteria, yeasts, fungi, and animal and plant cells, but also the cultivation of plants and the breeding of animals.

Figure 1:
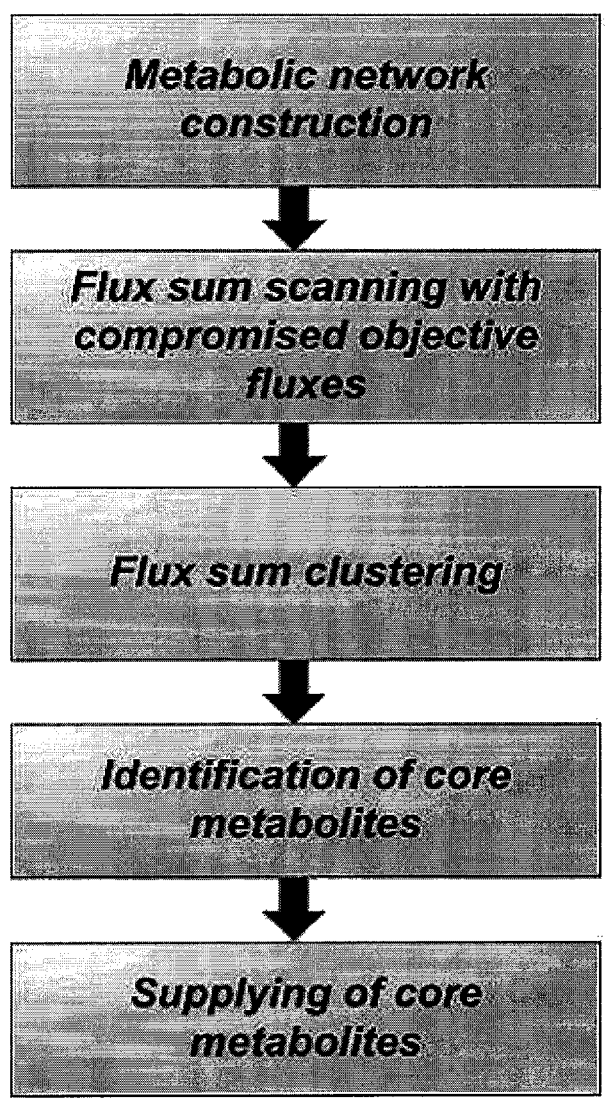
FIG. 1 is a schematic diagram of a method for increasing the production of a useful substance through the analysis of key metabolites according to the present invention.

FIG. 1 shows the concept of a method for increasing the production of a useful substance by the analysis of key metabolites using flux sum according to the present invention. Namely, the present invention provides a method for increasing the product yield of a useful substance by selecting a target organism producing the useful substance, constructing the metabolic network model of the selected organism, determining the flux sum values ($\Phi$) of metabolites in the constructed metabolic pathway network, perturbing the flux sum, and screening key metabolites involved in increasing the production yield of a useful target product by clustering and providing the key metabolites. The present invention will now be described in detail.

1. Metabolic Network Construction

In the present invention, a new metabolic flux analysis system was constructed using an *E. coli* mutant as a target strain for producing a useful substance. This system comprises most of the metabolic network of *E. coli*. For *E. coli*, new metabolic network consists of 979 biochemical reactions, and 814 metabolites are considered in the metabolic network. The biological composition of *E. coli* for use in biomass formation rate to be used as an objective function of metabolic flux analysis, was constructed as disclosed in the prior literature (Neidhardt et al., *E. coli* and *Salmonella*: Cellular and Molecular Biology, 1996).

2. Definition and Perturbation of Flux Sum (1) Flux Sum

If all the metabolites, their metabolic pathways and a corresponding stoichiometric matrix ($S_{ij}^T$; the stoichiometric coefficient of the $i^{th}$ metabolite in $j^{th}$ reaction with time) are known, a metabolic flux vector ($v_j$, the metabolic flux of j pathway) can be calculated, in which a change in metabolite concentration X with time can be expressed as the sum of the fluxes of all metabolic reactions. A change in X with time can be defined as the following equation under the assumption of a quasi-steady state:

$$S^T v = dX/dt = 0$$

wherein $S^T v$ is a change in X with time, X is metabolite concentration, and t is time.

Herein, the utilization of fluxes around metabolites is defined as follows in view of metabolites so as to correspond to metabolic fluxes defined in view of metabolic reactions.

Namely, the metabolic flux of a reaction where a relevant metabolite is consumed with respect to the $i^{th}$ metabolite is defined as $f_{in}$, and the metabolic flux of a reaction where a relevant metabolite is produced with respect to the $i^{th}$ metabolite is defined as $f_{out}$, and these metabolic fluxes are represented by Equations 2 and 3 below, respectively.

$$f_{in} = \sum_{j}^{ingoing} |S_{ij} v_j| \qquad [\text{Equation 2}]$$

$$f_{out} = \sum_{j}^{outgoing} |S_{ij} v_j| \qquad [\text{Equation 3}]$$

wherein $S_{ij}$ is the stoichiometric coefficient of the $i^{th}$ metabolite in the $j^{th}$ reaction, and $v_j$ is the metabolic flux vector of j pathway.

Figure 2:
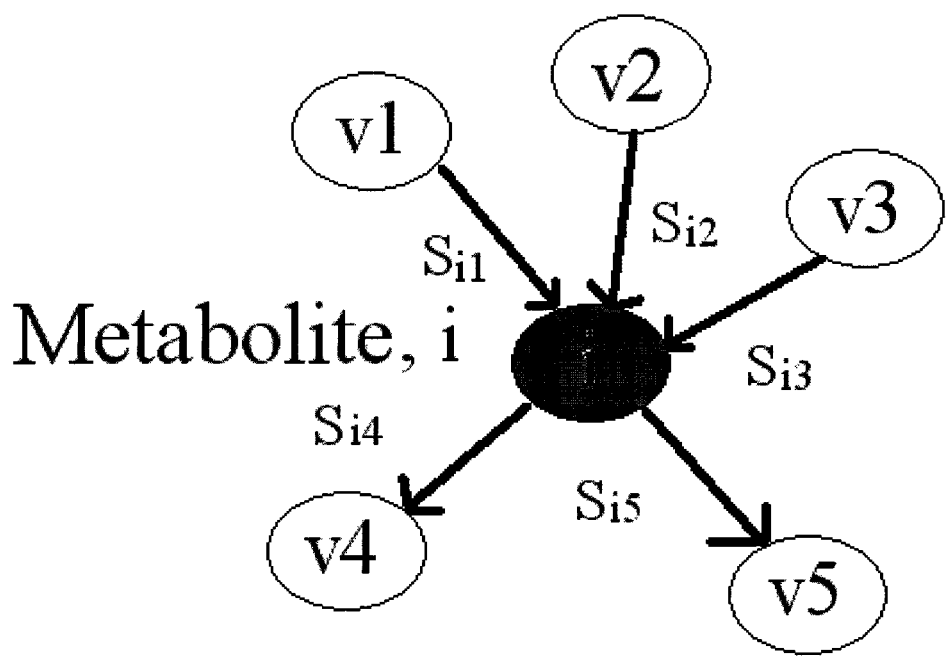
FIG. 2 shows an example of metabolic fluxes of a reaction equation, in which a relevant metabolite is consumed with respect to the $i^{th}$ metabolite.

FIG. 2 shows an example of the metabolic flux of a reaction where relevant metabolites are consumed with respect to the $i^{th}$ metabolite. The metabolic fluxes of the reactions shown in FIG. 2 can be defined as follows:

$$f_{in} = \sum_{j}^{ingoing} S_{ij} v_j = S_{i1} v_1 + S_{i2} v_2 + S_{i3} v_3$$

$$f_{out} = \sum_{j}^{outgoing} S_{ij} v_j = S_{i4} v_4 + S_{i5} v_5.$$

$f_{in}$ and $f_{out}$ defined above can be considered as the utilization of fluxes around metabolites, since they have the same absolute value under the assumption of a quasi-steady state. In the present invention, the utilization of fluxes around metabolites is named "flux sum" ($\Phi$) and defined as equation 1:

$$\Phi_i = |f_{in}| = |f_{out}| = 1/2 \sum_{j} |S_{ij} v_j| \qquad [\text{Equation 1}]$$

wherein $\Phi_i$ represents the utilization of the $i^{th}$ metabolite, $f_{in}$ represents the total metabolic flux of reactions where a relevant metabolite is consumed with respect to the $i^{th}$ metabolite, $f_{out}$ represents the total metabolic flux of reactions where a useful target product is produced with respect to the $i^{th}$ metabolite, $S_{ij}$ represents the stoichiometric coefficient of the $i^{th}$ metabolite in the $j^{th}$ reaction, $v_j$ represents the metabolic flux of j pathway.

Flux sum ($\Phi$) is an amount newly defined to express the utilization of metabolites, which have not been employed in the existing metabolic analysis method. The more the utilization of relevant metabolites is, the higher the value ($\Phi$)

becomes, and the less the utilization of relevant metabolites is, the lower the value ($\Phi$) becomes.

Generally, the existing metabolic flux analysis is based on the assumption of a quasi-steady state, and a change in the concentration of internal metabolites caused by a change in external environment is very immediate, and thus this change is generally neglected and it is assumed that the concentration of internal metabolites is not changed. Namely, the metabolic flux analysis method has a shortcoming in that the property of each metabolite cannot be examined, since a change in the concentration of internal metabolites caused by a change in external environment is very immediate, and thus this change is neglected, whereby it is assumed that the concentration of internal metabolites is not changed.

In the present invention, flux sum ($\Phi$) is defined as the utilization of metabolites so as to provide a quantitative base capable of finding key metabolites for increasing the production of a useful substance.

(2) Flux Sum Scanning with Compromised Objective Fluxes (Flux Sum SCOF)

It is possible to determine flux sum ($\Phi$) from the above definition and to determine flux sum ($\Phi$) for all metabolites on the basis of the above determined flux sum.

At this time, it is possible to examine a change in flux sum according to the perturbation of functions associated with the production of a useful substance. Herein, the profile of flux sum of internal metabolites according to a change in objective functions was examined.

When metabolic flux analysis is performed on the basis of linear programming, a plurality of objective functions is generally used to study a change in functions according to perturbation. Byproduct formation rate and biomass formation rate are mainly used as objective functions (Pharkya P et al., *Biotechnol Bioeng.*, 84:887, 2003). Linear programming that uses two or more objective functions as described above is called multiobjective linear programming.

Objective functions associated with the production of a useful substance, which can be applied to the present invention, may include product (useful substance) formation rate, specific growth rate, byproduct formation rate, substrate uptake rate, ATP formation rate, oxygen uptake rate, and the like. Multi-objective linear programming to be used herein can be transformed to linear programming having one objective function through the following algorithm defined as flux sum SCOF. Other functions are transformed, satisfying restriction conditions.

Step 1:

A plurality of objective functions is selected on the basis of the formation rate of specific useful substance. Any of the functions associated with the production of the useful substance, as described above, can be selected.

v cell objective function 1=product formation rate,
v cell objective function 2=specific growth rate,
v cell objective function 3=byproduct formation rate . . . .

Herein, mathematical representations through multiobjective linear programming are as follows.

Objective Functions:
maximize v cell objective function 3,
maximize v cell objective function 2,
maximize v cell objective function 1,
Restriction conditions:

$$\sum_{j \in J} S_{ij} v_j = b_i, \quad \forall i \in I$$

$$l_i \leq b_i \leq u_i, \quad \forall i \in E$$

$$\alpha_j \leq v_j \leq \beta_j, \quad \forall i \in J$$

wherein I is a set of metabolites, E is a set of external metabolites, J is a set of reactions, $S_{ij}$ is the stoichiometric coefficient of the $i^{th}$ metabolite in the $j^{th}$ reaction, $b_i$ is the net transport flux (+: product secretion; −: substrate intake; and 0: intermediate value) of the $i^{th}$ metabolite, $l_i$ and $u_i$ denote lower and upper limits, respectively, for the net transport flux of the $i^{th}$ metabolite, and $\alpha_j$ and $\beta_j$ denote lower and upper limits, respectively, for the flux of a reaction.

Step 2:

Each of the objective functions is maximized or minimized to determine the maximum value and minimum value of each of the functions.

$v_{min}$ cell objective function 1 < $v$ cell objective function 1 < $v_{max}$ cell objective function 1

$v_{min}$ cell objective function 2 < $v$ cell objective function 2 < $v_{max}$ cell objective function 2

$v_{min}$ cell objective function 3 < $v$ cell objective function 3 < $v_{max}$ cell objective function 3

. . . .

Step 3:

The multiobjective linear programming can be transformed to linear programming having one objective function through the following algorithm. The formation rate of the useful substance is set as a single objective function, and optimization is performed while increasing the product (useful substance) formation rate within a range between the minimum values and maximum values of other functions.

```
t1 = v_min cell objective function 2 ~ v_max cellll objective function 2
start
    t2 = v_min cell objective function 3 ~ v_max cell objective function 3
    start
        Maximize v_min cell objective function 1
        Subject to;
            ∑ S_ij v_j = b_i,   ∀ i ∈ I
            j∈J
            l_i ≤ b_i ≤ u_i,    ∀ i ∈ E
            α_j ≤ v_j ≤ β_j,    ∀ j ∈ J
            v cell objective function 2 = t1
            v cell objective function 3 = t2
    end
end
```

The above algorithm makes it possible to determine a metabolic flux space satisfying the considered objective functions.

Then, the flux sum ($\Phi$) value of all metabolites is determined from the profile of each of the objective functions. Herein, the formation rate of the useful substances is set as a main function of screening key metabolites, other functions influencing the production of the useful substances are variously applied to determine the profile of the product formation rate, and the flux sum ($\Phi$) of all the metabolites is determined from the profile, and an increase or decrease in the metabolites is examined.

3. Flux Sum Clustering Using Useful Substance Formation Rate and Specific Growth Rate as Objective Functions From the linear programming that uses two objective functions, that is, the profile consisting of useful substance formation rate and another function (e.g., specific growth rate), metabolites, which show an increase in flux sum ($\Phi$) with an increase in useful substance formation rate, can be clustered and screened.

Figure 3:
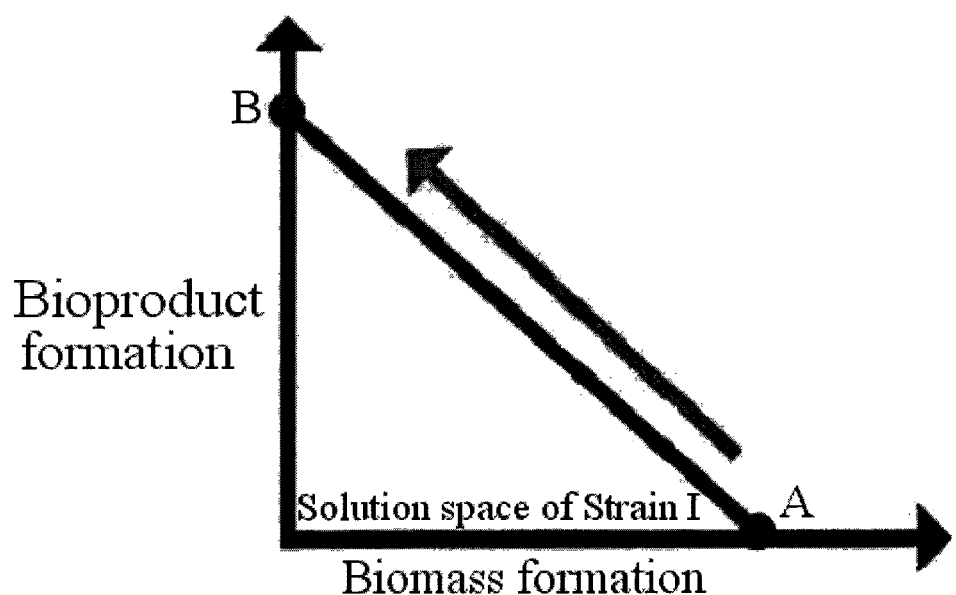
FIG. 3 shows a profile obtained when specific growth rate and the formation rate of a useful substance are used as a objective function.

For example, it is possible to determine the flux sum (Φ) of all internal metabolites using, as functions, the specific growth rate and useful substance formation rate of each point selected from a profile that includes specific growth rate and useful substance formation rate as objective functions, as shown in FIG. 3.

Then, from the profile of useful substance formation rate according to a function of specific growth rate as shown in FIG. 3, metabolites, which show an increase in flux sum (Φ) according to an increase in useful substance formation rate (A→B direction), are screened to find key metabolites.

Figure 4:
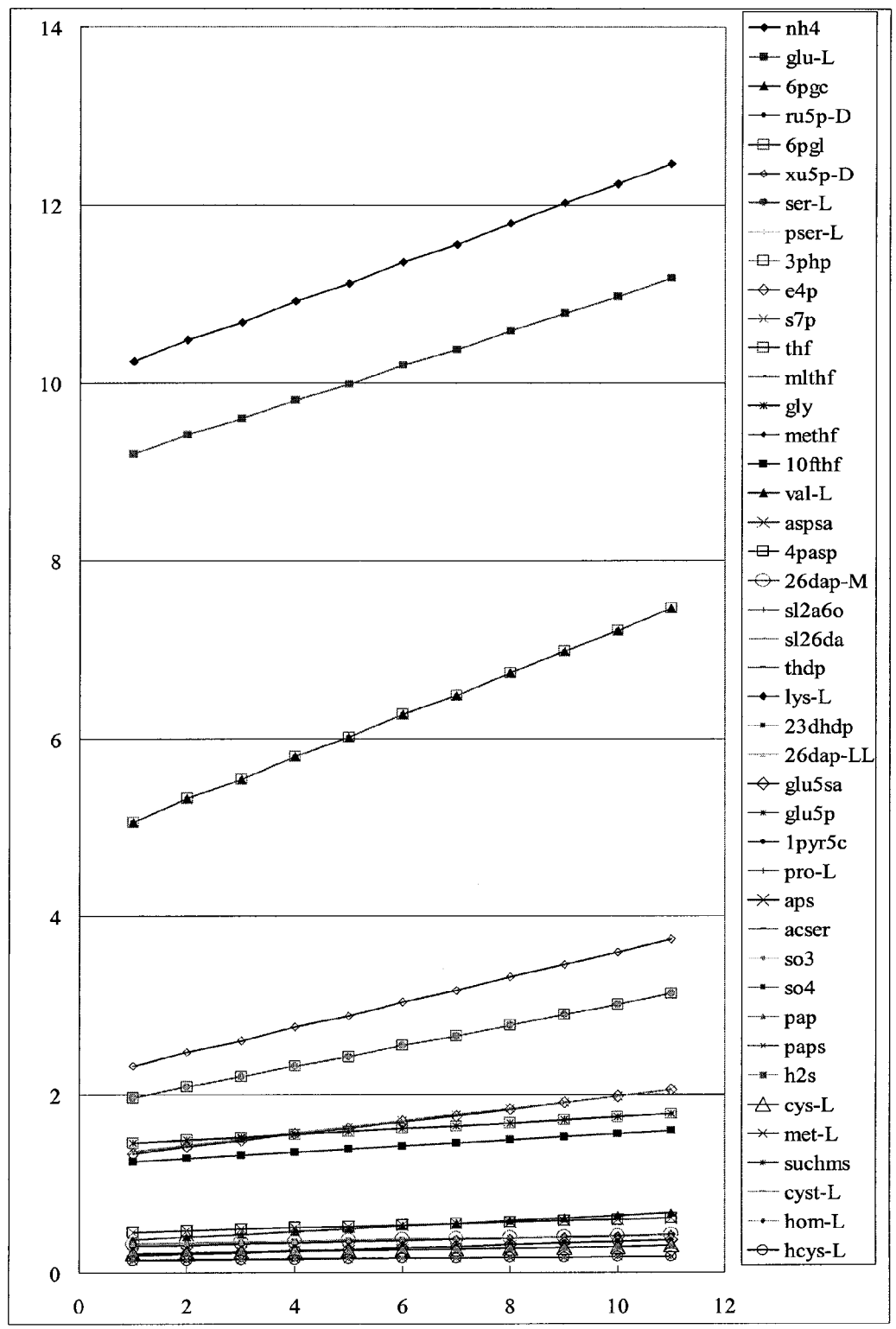
FIG. 4 shows the profile and list of metabolites which show an increase in flux sum ($\Phi$) (y-axis) with an increase in the formation rate of a useful substance (x-axis).

The metabolites that show an increase in flux sum (Φ) with an increase in useful substance formation are screened according to the above described method and shown in FIG. 4. FIG. 4 shows a profile of the flux sum (y-axis) of each metabolite for useful substance formation rate (x-axis), and a list of the metabolites. The increase (Φ) in flux sum with the increase in useful substance formation rate indicates that the utilization of relevant metabolites increases as a useful substance is formed.

Also, it is possible to perform multiobjective linear programming that uses three or more objective functions, including specific growth rate, useful substance formation rate and unnecessary by useful substance formation rate. The flux sum (Φ) of all internal metabolites can be determined from a profile resulting from the aforementioned multiobjective linear programming that uses three objective functions, and a group of metabolites, which show an increase in the utilization of relevant metabolites according to the formation of useful substance and have little amount of unnecessary byproducts, can be screened from the profile.

Figure 5:
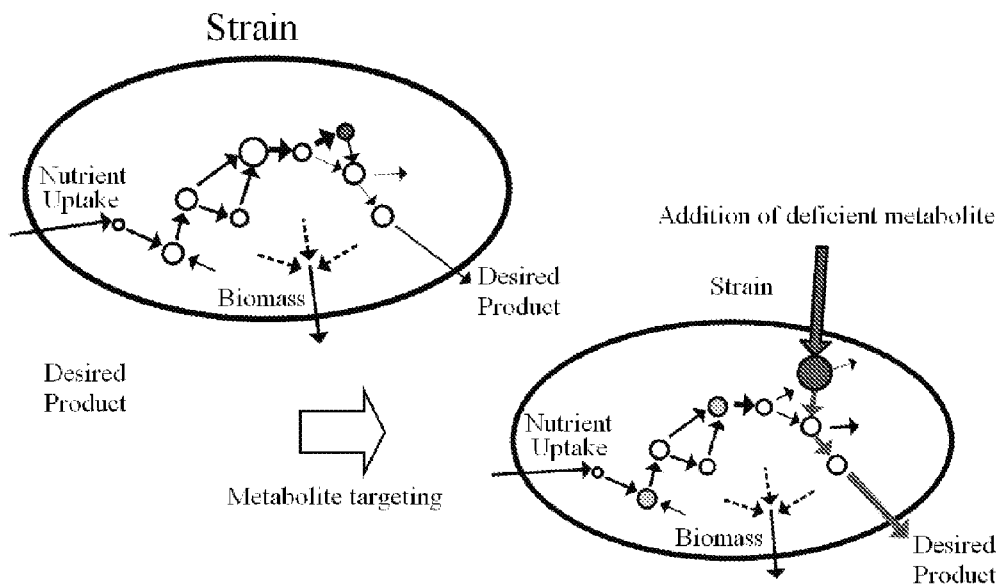
FIG. 5 is a schematic diagram showing that useful metabolites are increased by adding metabolites from the outside.

4. Experimental Analysis for Productivity Improvement: Supply of Metabolites from the Outside Useful substance formation rate is set as a main function, other functions influencing the production of useful substances are variously applied, and flux sum SCOF, an algorithm perturbing the functions, is performed to determine the profile of the objective function. From the profile, the flux sum (Φ) of all metabolites is determined, and a group of metabolites, which show an increase in flux sum (Φ) with an increase in useful substance formation rate, is screened. The increase (Φ) in flux sum with the increase in product formation rate indicates that the utilization of relevant metabolites increases according to the formation of useful substances. Thus, it is possible to increase flux sum by introducing and/or amplifying genes associated with metabolites and adding deficient metabolites from the outside of cells (see FIG. 5).

When genes that produce or consume the screened key metabolites are introduced and/or amplified, it is possible to increase the utilization of the relevant metabolites.

Figure 6:
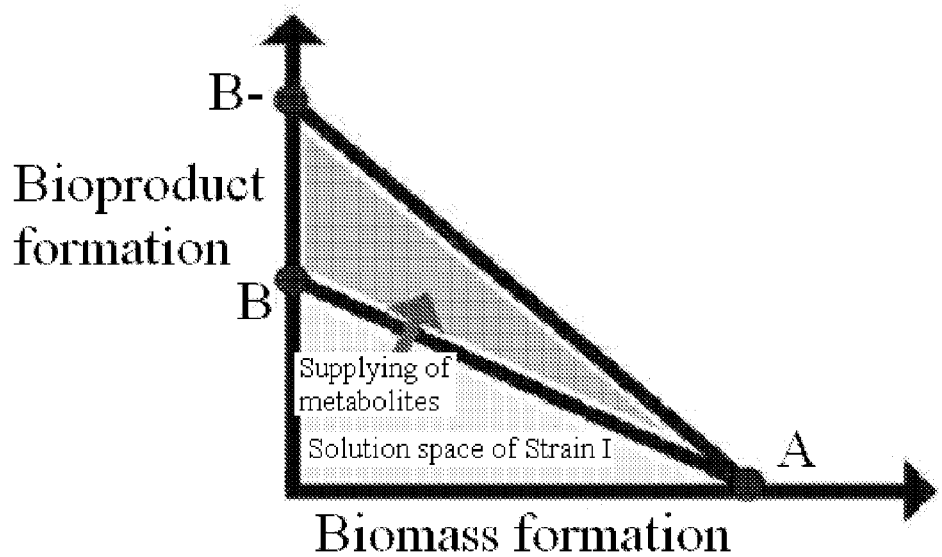
FIG. 6 is a schematic diagram showing that the maximum value of the formation rate of a useful substance is increased when metabolites are added from the outside.

Supplying specific metabolites from the outside as shown in FIG. 6 serves to increase a space toward useful substances in a metabolic flux space. Specifically, the external supply of relevant metabolites increases the original metabolic flux space, and particularly increases the metabolic flux space toward useful substances. Thus, it is possible to increase the production of useful substances by identifying metabolites important in the production of useful substances and supplying the relevant metabolites from the outside.

Herein, whether the relevant strain can uptake relevant metabolites should be examined, and this can be achieved through a variety of databases and literature. In particular, if a transporter that can uptake relevant metabolites exists, relevant metabolites can be added to a media in an actual culture experiment, and the production of useful substances can be finally analyzed.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof. Those skilled in the art will appreciate that simple modifications, variations and additions to the present invention are possible, without departing from the scope and spirit of the invention as disclosed in the accompanying claims.

INDUSTRIAL APPLICABILITY

As described in detail above, according to the present invention, the metabolic utilization (flux sum; Φ) of specific metabolites according to an increase in useful substance formation rate can be predicted, so that key metabolites in increasing the production of a useful substance can be screened. Also, it is possible to increase the production of a useful substance through the method of improving a target organism by introducing and/or amplifying genes associated with the screened metabolites or through the method of supplying the metabolites in the cultivation of the organism.

What is claimed is:

1. A method for improving an organism producing a useful substance, the method comprising the steps of:
   (a) selecting a target organism for producing a target useful substance, and constructing a metabolic network model of the selected target organism;
   (b) defining a utilization of each of i metabolites in j reactions as a flux sum $$\Phi_i = \frac{1}{2} \sum_j |S_{ij} v_j|,$$

wherein $\Phi_i$ represents the utilization of the $i^{th}$ metabolite, $S_{ij}$ represents the stoichiometric coefficient of the $i^{th}$ metabolite in the $j^{th}$ reaction under the assumption of a quasi-stead state, and $v_j$ represents the metabolic flux vector of the $j^{th}$ reaction;
   (c) selecting a plurality of objective functions, including a function of the formation rate of the useful substance, and additional objective functions other than the formation rate of the useful substance
   (d) determining a minimum value and a maximum value of the additional objective functions
   (e) optimizing the objective function of the formation rate of the useful substance within the range between the minimum value and the maximum value of the additional objective functions,
   (f) determining the flux sum ($\Phi_i$) of each metabolite from the objective functions;
   (g) clustering and screening a specific metabolite which shows an increase in the flux sum ($\Phi_i$) according to an increase in the formation rate of the target useful substance;
   (h) selecting genes to be introduced or amplified from a metabolic pathway associated with the specific metabolite screened in the step (g); and
   (i) constructing a mutant of the target organism by introducing and/or amplifying the genes selected in the step (h) in the target organism.

2. The method for improving the organism producing the useful substance according to claim 1, which additionally comprises a step of: (j) experimentally confirming the production of the useful substance by culturing the mutant constructed in the step (i).

3. The method for improving the organism producing the useful substance according to claim 1, wherein the additional objective functions involved in the production of the useful substance in the step (c) is one or more selected from the group consisting of specific growth rate, byproduct formation rate, substrate uptake rate, ATP formation rate and oxygen uptake rate.

4. The method for improving the organism producing the useful substance according to claim 1, wherein the additional objective function involved in the production of the useful substance in the step (c) is specific growth rate.

5. The method for improving the organism producing the useful substance according to claim 1, wherein the target organism is a microorganism.

6. The method for improving the organism producing the useful substance according to claim 1, wherein the useful target substance is a primary metabolite, a secondary metabolite or a foreign protein, and the target organism is a microorganism capable of producing a primary metabolite, a secondary metabolite or a foreign protein.

* * * * *

UNITED STATES PATENT AND TRADEMARK OFFICE
CERTIFICATE OF CORRECTION

PATENT NO.        : 8,594,945 B2                    Page 1 of 1
APPLICATION NO.   : 12/299223
DATED             : November 26, 2013
INVENTOR(S)       : Sang-Yup Lee et al.

It is certified that error appears in the above-identified patent and that said Letters Patent is hereby corrected as shown below:

In the Claims

Claim 3, Column 11, Line 7 through Line 8: change "substance in the step (c) is one or more selected from the group consisting of specific growth rate, byproduct formation" to --substance in the step (c) include one or more of specific growth rate, byproduct formation--

Claim 4, Column 11, Line 13: change "objective function involved in the production of the useful" to --objective functions involved in the production of the useful--

Claim 4, Column 11, Line 14: change "substance in the step (c) is specific growth rate." to --substance in the step (c) include specific growth rate.--

Signed and Sealed this
Thirteenth Day of May, 2014

Michelle K. Lee
*Deputy Director of the United States Patent and Trademark Office*